United States Patent [19]

Samuels et al.

[11] Patent Number: 5,478,541
[45] Date of Patent: Dec. 26, 1995

[54] SEPARATELY REMOVING MERCAPTANS AND HYDROGEN SULFIDE FROM GAS STREAMS

[76] Inventors: Alvin Samuels, 444 Fairway Dr., New Orleans, La. 70124; Irwin Fox, 623 Old Slave Rd., Chesterfield, Mo. 63005

[21] Appl. No.: 440,114

[22] Filed: May 12, 1995

Related U.S. Application Data

[63] Continuation-in-part of Ser. No. 187,146, Jan. 27, 1994, abandoned.

[51] Int. Cl.$^6$ .............................. C01B 17/16; C01B 17/20
[52] U.S. Cl. ....................... 423/220; 423/231; 423/244.1; 423/245.1; 423/443; 423/562
[58] Field of Search ........................ 423/220, 231, 423/244.1, 245.1, 443, 562, 573.1

[56] References Cited

U.S. PATENT DOCUMENTS

| | | | |
|---|---|---|---|
| 2,850,352 | 9/1958 | Odell | 23/2 |
| 2,882,224 | 4/1959 | Gleim et al. | 208/206 |
| 2,966,453 | 12/1960 | Gleim et al. | 208/206 |
| 3,391,988 | 7/1968 | Friess | 23/2 |
| 3,574,093 | 4/1971 | Strong | 208/206 |
| 3,923,645 | 12/1975 | Anderson et al. | 208/206 |
| 4,009,251 | 2/1977 | Meuly | 423/573 G |
| 4,072,480 | 2/1978 | Wagner | 55/73 |
| 4,090,954 | 5/1978 | Ward | 208/206 |
| 4,246,244 | 1/1981 | Fox | 423/225 |
| 4,256,728 | 3/1981 | Nishino et al. | 422/4 |
| 4,311,680 | 1/1982 | Frech et al. | 423/230 |
| 4,422,958 | 12/1983 | Dupin | 502/217 |
| 4,491,563 | 1/1985 | Reusser et al. | 422/5 |
| 4,552,734 | 11/1985 | Iannicelli et al. | 423/230 |
| 4,552,735 | 11/1985 | Iannicelli et al. | 423/224 |
| 4,774,067 | 9/1988 | Voirin et al. | 423/244 |
| 4,875,997 | 10/1989 | Langford | 208/235 |
| 5,244,643 | 9/1993 | Verachtert | 423/243.08 |
| 5,264,194 | 11/1993 | Fox et al. | 423/231 |
| 5,320,992 | 6/1994 | Fox et al. | 502/84 |

OTHER PUBLICATIONS

"Mercaptan Removal Rate Exceeds 99% at Canadian Gas Plant" by Bill Judd Oil and Gas Journal 10 Aug. 1993 pp. 81–83.

"$H_2S$ Removal System Shows Promise Over Iron Sponge" by Alvin Samuels Oil and Gas Journal of Feb. 1990 Penn Well Publishing Co.

*Primary Examiner*—Gary P. Straub
*Assistant Examiner*—Timothy C. Vanoy
*Attorney, Agent, or Firm*—Jerome A. Gross

[57] ABSTRACT

The present invention provides a method for separately removing mercaptans and hydrogen sulfide from a hydrocarbon gas stream by passing the gas through a bed which includes iron oxide which catalyzes the formation of disulfides and trisulfides from mercaptans and also reacts with at least part of the hydrogen sulfide to form acid-stable solids; causing the di- and trisulfides to exit the bed in the gas phase; and removing and recovering the di- and trisulfides by adsorption or condensation. Any remaining hydrogen sulfide may be scavenged from the gas stream by passage through a bed containing iron oxide similar to that used first above. If the gas stream contains substantial amounts of hydrocarbon aerosols, they should be filtered out in advance of the bed.

6 Claims, No Drawings

SEPARATELY REMOVING MERCAPTANS AND HYDROGEN SULFIDE FROM GAS STREAMS

CROSS-REFERENCE TO RELATED APPLICATIONS

The present application is a continuation-in-part of U.S. patent application Ser. No. 08/187,146, filed Jan. 27, 1994 and duly allowed; to be abandoned.

BACKGROUND OF THE INVENTION

The present invention teaches how to remove mercaptans from hydrocarbon gas streams also containing hydrogen sulfide with subsequent recovery of disulfides and trisulfides.

DESCRIPTION OF RELATED ART

Reduced sulfur compounds are often found in gas streams associated with petroleum storage and transfer facilities, sewage treatment plants and pulp and paper mills. Among the most common of these compounds are hydrogen sulfide, which has the odor of rotten eggs and is toxic and corrosive; and mercaptans, especially methyl and ethyl mercaptans, which have very pungent and undesirable odors. It is desirable to remove these compounds prior to further processing or transporting to prevent atmospheric pollution and to protect workers and equipment.

Most methods for removing reduced sulfur compounds are primarily directed at hydrogen sulfide, and some of the most widely used hydrogen sulfide removal processes, such as amine scrubbing, are not particularly efficient in removing mercaptans. Mercaptan removal processes shown in the prior art either oxidize mercaptans to disulfides or to sulfur dioxide as the first step in a Clause sulfur recovery process (U.S. Pat. No. 4,422,958), or to sulfates or sulfonates (U.S. Pat. Nos. 4,552,734 and 4,552,735), or absorb them onto such adsorbents as treated activated carbon (U.S. Pat. Nos. 4,256,728 or 4,072,480). Mercaptan oxidation to disulfides is well known, but is usually carried out by contacting the mercaptan-containing gas stream with an oxidation catalyst and an oxidation agent such as oxygen in an aqueous alkaline solution. Variations of such catalysts are shown in U.S. Pat. Nos. 5,244,643 (sulfonated metal phthalocyanine), 4,491,563 (nickel oxide with oxide of a rare earth metal), 4,311,680 (oxides of iron, chromium, cobalt, lead, manganese, molybdenum, nickel, copper, vanadium zinc, tungsten or antimony), or 2,966,453 (porphyrin).

Application of these processes to many industrial situations has involved difficult problems in practice. For example, since it is often desirable to remove both hydrogen sulfide and mercaptans from gas streams, it would be advantageous to be able to remove both by using only one type of reactant or catalytic agent. Often, however, the known mercaptan removal processes remove hydrogen sulfide inefficiently or not at all.

Additionally, since most mercaptan conversion catalysts which are used in dry beds are supported on inert particulate materials, it is important to keep their surfaces unfouled. However, condensation of the higher-boiling disulfides formed from mercaptans can coat such particulates, thus reducing their activity and their capacity for removing both mercaptans and hydrogen sulfide.

Finally, it has been difficult to recover pure streams of disulfides in prior art methods without extensive processing. (See, for example, Mercaptan removal rate exceeds 99% at Canadian gas plant, by B. Judd, *Oil & Journal*, p. 81–83 (Aug. 16, 1993). Disulfides formed when mercaptans are oxidized in aqueous alkaline solution have higher affinity for an organic phase and can be extracted from the aqueous phase by a hydrocarbon, but handling of the separate liquid phase and recovery of relatively pure disulfides from the aqueous/organic mixture requires much additional equipment.

Thus, a method to separately remove hydrogen sulfide and mercaptans, from a gas stream by using only a single type of reactive or catalytic agent which allowed for the recovery of economically valuable disulfides and minimized the fouling of the reactive or catalytic agent would be very advantageous.

SUMMARY OF THE INVENTION

These advantages and others are provided by the process of the present invention which separately removes mercaptans and at least part of any hydrogen sulfide from a hydrocarbon gas stream by: providing a bed containing moistened particles including iron oxide of the type which is not only reactive to hydrogen sulfide but which also catalyzes the formation of disulfides and trisulfides from mercaptans; passing the gas stream into and through the bed, and in so doing, converting the mercaptans to disulfides and trisulfides and reacting at least part of any hydrogen sulfide to solid products which remain in the bed; causing the gas stream to exit from the bed while the disulfides and trisulfides remain therein in substantially gaseous phase; and removing the disulfides and trisulfides from the gas stream.

For gases in which the content of hydrogen sulfide is higher than the content of mercaptans, an additional step may be added to scavenge the hydrogen sulfide. The added step includes passing the gas stream from which disulfides and trisulfides have been removed through means to scavenge remaining hydrogen sulfide therefrom. This step may simply be a repetition of the first two steps described above which involve providing a bed containing moistened particles including iron oxide and passing the gas stream therethrough to remove remaining hydrogen sulfide.

If the gas stream contains substantial amounts of hydrocarbon aerosol or liquid hydrocarbons, a suitable filter should be imposed in the stream in advance of the bed.

DESCRIPTION OF THE PREFERRED EMBODIMENTS

Gases containing mercaptans and various levels of hydrogen sulfide may be the low molecular weight hydrocarbons such as methane, ethane and propane. Such gases may also contain oxygen, nitrogen and other compounds. Depending on the source of the gas, hydrogen sulfide may be present at levels higher or lower than the mercaptans. Gases escaping from crude oil loading or transfer facilities (especially when the oil has been previously treated by one of the common sulfur removal processes) often contain five or six times as much mercaptans as hydrogen sulfide, with mercaptan levels of up to 700 ppm. being common.

In the process of the present invention, a gas stream containing mercaptans and hydrogen sulfide is first contacted with a reactive iron oxide of the type which (a) reacts with hydrogen sulfide to form products which are environmentally stable, and (b) also catalyzes the formation of disulfides and trisulfides from volatile mercaptans, specifically methyl and ethyl mercaptan. Since it is desirable to minimize the pressure drop when gas is pumped through beds of the iron oxide material, the iron oxide should preferably be in particulate form and supported on larger particles of a rigid inert mineral material.

We have found the iron oxide which was disclosed in U.S. Pat. No. 4,246,244 to be preferred, especially when supported on sized particles of calcined montmorillonite clay. That oxide, whose particles are composed of a crystalline phase of $Fe_3O_4$, together with an amorphous $Fe_2O_3$ moiety, has a surface area of at least 4.0 $m^2/g$. It is available commercially, in a preparation having about 20 lb. of iron oxide per cubic foot of inert support material, as SULFATREAT, available from Gas Sweetener Associates, St. Louis, Mo.

As the gas passes through the bed under conditions which will be defined below, the iron oxide catalyzes the conversion of mercaptans, especially methyl and ethyl mercaptan, to disulfides and trisulfides which pass out of the bed substantially quantitatively in the gas phase. Such disulfides and trisulfides formed from methyl and ethyl mercaptans are typically dimethyl disulfide, ethyl-methyl disulfide, diethyl disulfide, and analogous alkyl trisulfides (hereinafter referred to collectively as "di- and trisulfides" or "disulfides and trisulfides"). Presumably, other volatile alkyl and aryl mercaptans would be similarly converted. While this reaction is taking place, the iron oxide also reacts with hydrogen sulfide to form products which are stable under environmental conditions. As described in U.S. Pat. No. 4,246,244 to one of the present inventors, such products are typically $FeS_2$, $S°$, $Fe_3O_4$, and other acid-stable, non-FeS iron sulfide species. Thus, while the iron oxide catalyzes the formation of di- and trisulfides from mercaptans, it is also being consumed by reacting with hydrogen sulfide.

The rate of conversion of mercaptans to di- and trisulfides appears to be substantially the same as the reaction of iron oxide with hydrogen sulfide. Thus, when hydrogen sulfide is present at lower concentrations than mercaptans, a bed designed to completely transform mercaptans to di- and trisulfides will also substantially remove hydrogen sulfide from the gas stream. Conversely, if hydrogen sulfide is present in higher concentrations than mercaptans, a bed designed to completely convert the mercaptans may permit some unreacted hydrogen sulfide to pass through the bed.

We have learned that it is very important to operate the first bed (which converts mercaptans to di- and trisulfides) under conditions which allow substantially all of the di- and trisulfides to exit the bed in the gas phase. This prevents di- and trisulfides from condensing on and coating or otherwise fouling, the supported iron oxides and thereby maintains their capacity or effectiveness. Maintaining the di- and trisulfides in the gas phase also allows their removal from the gas stream separately from the removal of hydrogen sulfide. It is also important to operate the bed in downflow mode to minimize the accumulation of liquid in the bed.

Further, the gas stream should preferably not include substantial quantities of hydrocarbon aerosols or liquid hydrocarbons; their presence may create a catalytic reaction with the reaction products previously generated, which may cause the generation of excessive temperatures. Installation of a suitable filter in the gas supply line in advance of the reactor bed will overcome this problem. Suitable filters may be obtained from several sources throughout the United States, for example the Ultisep brand coalescing filter, obtainable from Porous Media Co. of St. Paul, Minn.

The following tests have been run to determine conditions which give the desired result for operation of the conversion bed.

EXAMPLE 1

A standard feed gas was prepared for use in all tests with a composition given below:

| Component | Concentration (vol. %) |
| --- | --- |
| Carbon dioxide | 4.97% |
| Nitrogen | 54.9 |
| Oxygen | 1.52 |
| Methane | 34.18 |
| Ethane | 0.89 |
| Propane | 1.44 |
| Butane | 1.65 |
| Pentane | 0.39 |
| Hexane | 0.04 |
| Heptanes+ | 0.02 |

Before feeding the gas to a bed, it was saturated with water at 20° C., with sulfur compounds added to this gas. The feed gas at 112 KPa, with sulfur compounds added in levels shown below, was fed at 0.030 SCF/min. and 18° C. to a 0.906" ID column of 2' height packed with SULFATREAT. Superficial gas velocity was 6.7 ft./min. After reaching stable operating conditions, composition of the inlet and outlet gas (given as 20 ppm. by volume) was as shown:

| Gas Components Concentration | Inlet Concentration | Outlet |
| --- | --- | --- |
| hydrogen sulfide | 47 | 8 |
| methyl mercaptan | 865 | 260 |
| ethyl mercaptan | 619 | 155 |
| dimethyl disulfide | 57 | 169 |
| methyl-ethyl disulfide | 90 | 420 |
| diethyl disulfide | 82 | 515 |
| dimethyl trisulfide | 41 | 49 |
| methyl-ethyl trisulfide | 62 | 83 |
| diethyl trisulfide | 37 | 79 |

Summarizing, hydrogen sulfide and mercaptan levels were reduced with a concomitant increase in levels of di- and trisulfides; however, a significant amount of sulfur products did not leave the bed with the gas stream, but remained in the bed.

EXAMPLE 2

A column of 0.906" ID and 2' in height was packed with SULFATREAT. Standard feed gas having the composition given in Example 1, and containing sulfur compounds in levels shown below, was fed into the top of the column at 15° C. and 15 KPa pressure at a flow rate of 0.00473 SCF/min., resulting in a superficial gas velocity of 1.06 ft./min. After reaching stable operating conditions, composition of the inlet and outlet gas (given as ppm. by volume) was as shown:

| Gas Component | Inlet Concentration | Outlet Concentration |
| --- | --- | --- |
| hydrogen sulfide | 152 | 1 |
| methyl mercaptan | 438 | 1 |
| ethyl mercaptan | 276 | 1 |
| dimethyl disulfide | 12.6 | 57 |
| methyl-ethyl | 2.2 | 134 |

| Gas Component | Inlet Concentration | Outlet Concentration |
|---|---|---|
| disulfide | | |
| diethyl disulfide | 33.7 | 189 |
| dimethyl trisulfide | 37.7 | 202 |
| methyl-ethyl trisulfide | 17.9 | 388 |
| diethyl trisulfide | 9.4 | 227 |

During the run there was negligible accumulation of sulfur in the column and substantially all of the mercaptans were converted to di- and trisulfides which exited the column in the gas phase.

It is obvious that many variables affect the performance characteristics of the first bed; with temperature, pressure, gas composition, gas velocity, residence time in the bed, type of bed packing, and reactivity of the iron oxide being some of the more obvious. While we cannot predict a priori which combination of these variables will provide the desired result of substantially total conversion of mercaptans with substantially all of the di- and trisulfides exiting the bed in the gas phase, Example 2 shows that simple variations in testing will readily provide workable proportions and conditions to accomplish this result.

Following the conversion step, the di- and trisulfides are removed from the gas stream by methods well known in the art. For example, the di- and trisulfides may either be condensed and recovered as a substantially pure liquid stream, or adsorbed onto a solid adsorbent, preferably activated carbon. If activated carbon is used, the di- and trisulfides may be recovered and the activated carbon regenerated by well known techniques such as steam stripping or by extraction with a solvent with a high affinity for the di- and trisulfide oils. Recovered di- and trisulfides may be sold or may be added back to a liquid hydrocarbon as desired.

Since the affinity of activated carbon for di- and trisulfides is very high, gas velocities in a carbon bed may be much higher than those in an iron oxide bed. Thus, a carbon column may be of smaller diameter than the mercaptan converting bed needed for a given gas stream.

If a significant amount of hydrogen sulfide remains in the gas stream exiting the conversion step, it may still be possible to use activated carbon for di- and trisulfide removal since the affinity of activated carbon for di- and trisulfides is greater than for hydrogen sulfide. In this case, however, the carbon column must be designed to adsorb all of the di- and trisulfides while passing through substantially all of the hydrogen sulfide.

Alternatively, preferential condensation of the di- and trisulfides without condensing hydrogen sulfide could accomplish the same separation. Selection of a condenser is easily done by one skilled in the art since the boiling points of the di- and trisulfides (109.7° C. for dimethyl disulfide, and 154° C. for diethyl disulfide) are significantly higher than that of hydrogen sulfide (−60.7° C.). The condenser design may be any conventional type such as shell-and-tube, plate-type, or flash chiller type. The di- and trisulfides may even be condensed by direct contact with a stream of liquid such as a hydrocarbon liquid.

When hydrogen sulfide remains in the gas after the conversion and di- and trisulfide removal steps, it may be scavenged by passing the gas stream through a final iron oxide bed. The iron oxide used in the final bed may be the same as is used in the bed for the conversion step, preferably as in the SULFATREAT material described above. Alternatively, any adsorbent or reactant which removes hydrogen sulfide from a gas stream could be used.

The present invention permits users to purchase and stock only one type of agent which cannot only catalyze the conversion of mercaptans but can also react with hydrogen sulfide to form environmentally stable end products. Previously, it was not known how to carry out separate removal of hydrogen sulfide and mercaptans with use of a single reactive/catalytic agent.

Additionally, the process of the present invention permits the recovery of di- and trisulfides in a relatively pure and separate stream without extensive further processing. The recovered di- and trisulfide oils may then be sold, added back to a liquid hydrocarbon stream or disposed of as most advantageous.

Finally, by causing the di- and trisulfides to pass through the mercaptan converting bed in gaseous form, coating of the bed particles is reduced and the reactive capacity of the iron oxide is extended.

As various modifications may be made in the procedures herein described and illustrated without departing from the scope of the invention, it is intended that all matter contained in the foregoing description shall be taken as illustrative rather than limiting.

We claim:

1. A process for removing mercaptans and at least a portion of the hydrogen sulfide from a hydrocarbon gas stream, comprising the steps of:

a. providing a bed containing moistened particles supporting a particulate form of iron oxide composed of a crystalline phase of $Fe_3O_4$ together with an amorphous $Fe_2O_3$ moiety having a surface area of at least 4.0 $m^2/g$, b. passing the gas stream into and through the bed, and in so doing, converting the mercaptans to gaseous disulfides and trisulfides, and reacting at least part of any hydrogen sulfide to solid products which remain in the bed, c. causing the gas stream to exit from the bed while the disulfides and trisulfides remain in substantially gaseous phase, and d. removing the disulfides and trisulfides from the gas stream.

2. The process defined in claim 1, further comprising the subsequent step of recycling the gas stream from which disulfides and trisulfides have been removed back through steps a and b of claim 1.

3. The process defined in claim 1, wherein step d comprises adsorbing the disulfides and trisulfides onto a bed of activated carbon from which the disulfides and trisulfides can be subsequently recovered by desorption.

4. The process defined in claim 1, wherein the step involving removing the disulfides and trisulfides from the gas stream comprises passing the gas stream into a bed of activated carbon, adsorbing substantially all of the disulfides and trisulfides onto the the activated carbon while passing substantially all of the hydrogen sulfide remaining in the gas stream through such bed, and regenerating the activated carbon and recovering the adsorbed disulfides and trisulfides.

5. The process defined in claim 1, wherein the step involving removing the disulfides and trisulfides from the gas stream comprises causing the disulfides and trisulfides in the gas stream to condense to form a liquid while permitting substantially all hydrogen sulfide remaining in the gas stream to remain in gaseous phase.

6. The process for removing mercaptans and at least a portion of the hydrogen sulfide from a hydrocarbon gas stream which includes some liquid or aerosol hydrocarbons, comprising the process as defined in claim 1, together with the preliminary step of filtering from the gas stream such liquid or aerosol hydrocarbons.

* * * * *